United States Patent

Sakaguchi et al.

[11] Patent Number: 5,807,246
[45] Date of Patent: Sep. 15, 1998

[54] DISPLAY DEVICE IN MEDICAL EXAMINATION AND TREATMENT SYSTEM

[75] Inventors: Nobuhiro Sakaguchi; Yoshio Uejima, both of Kyoto, Japan

[73] Assignee: Nellcor Puritan Bennett Incorporated, Pleasanton, Calif.

[21] Appl. No.: 256,157

[22] PCT Filed: Dec. 28, 1992

[86] PCT No.: PCT/JP92/01737

§ 371 Date: Jul. 3, 1995

§ 102(e) Date: Jul. 3, 1995

[87] PCT Pub. No.: WO93/12711

PCT Pub. Date: Jul. 8, 1993

[30] Foreign Application Priority Data

Dec. 28, 1991 [JP] Japan .................................. 3-112931

[51] Int. Cl.⁶ .................................................. A61B 5/00
[52] U.S. Cl. ........................ 600/310; 600/322; 600/323
[58] Field of Search .......................... 128/630, 650–651, 128/660.04, 660.02, 660.689, 664–667, 709, 632–633; 349/9, 5–7; 600/101, 103, 109, 113

[56] References Cited

U.S. PATENT DOCUMENTS 3,978,470  8/1976  McGuire ................................. 340/324
4,051,522  9/1977  Healy et al. .............................. 358/86
4,154,231  5/1979  Russell ................................... 128/633
4,733,383  3/1988  Waterbury .

FOREIGN PATENT DOCUMENTS

A-60475/86   1/1987   Australia .
A-77184/87   2/1988   Australia .
   202 983  12/1983   German Dem. Rep. .
23 59 740 A1 12/1975  Germany .

Primary Examiner—Robert L. Nasser
Assistant Examiner—Ryan Carter
Attorney, Agent, or Firm—Townsend and Townsend and Crew LLP

[57] ABSTRACT

A pulse oximeter display device which displays oxygen saturation data is provided. The device comprises a multi-color display unit which displays oxygen saturation data in first and second colors. A display drive is coupled to the display unit, and a control unit is coupled to the display drive. Limits for oxygen saturation data are set by the control unit. The control unit further provides three signals to the display drive. The first signal is provided to continuously illuminate the display in the first color if the oxygen saturation data is within the limits. The second signal is provided to intermittently illuminate the display unit in the second color if the oxygen saturation data is not within the limits. The third signal is provided to continuously illuminate the display unit in the second color if the limits have not been set.

3 Claims, 4 Drawing Sheets

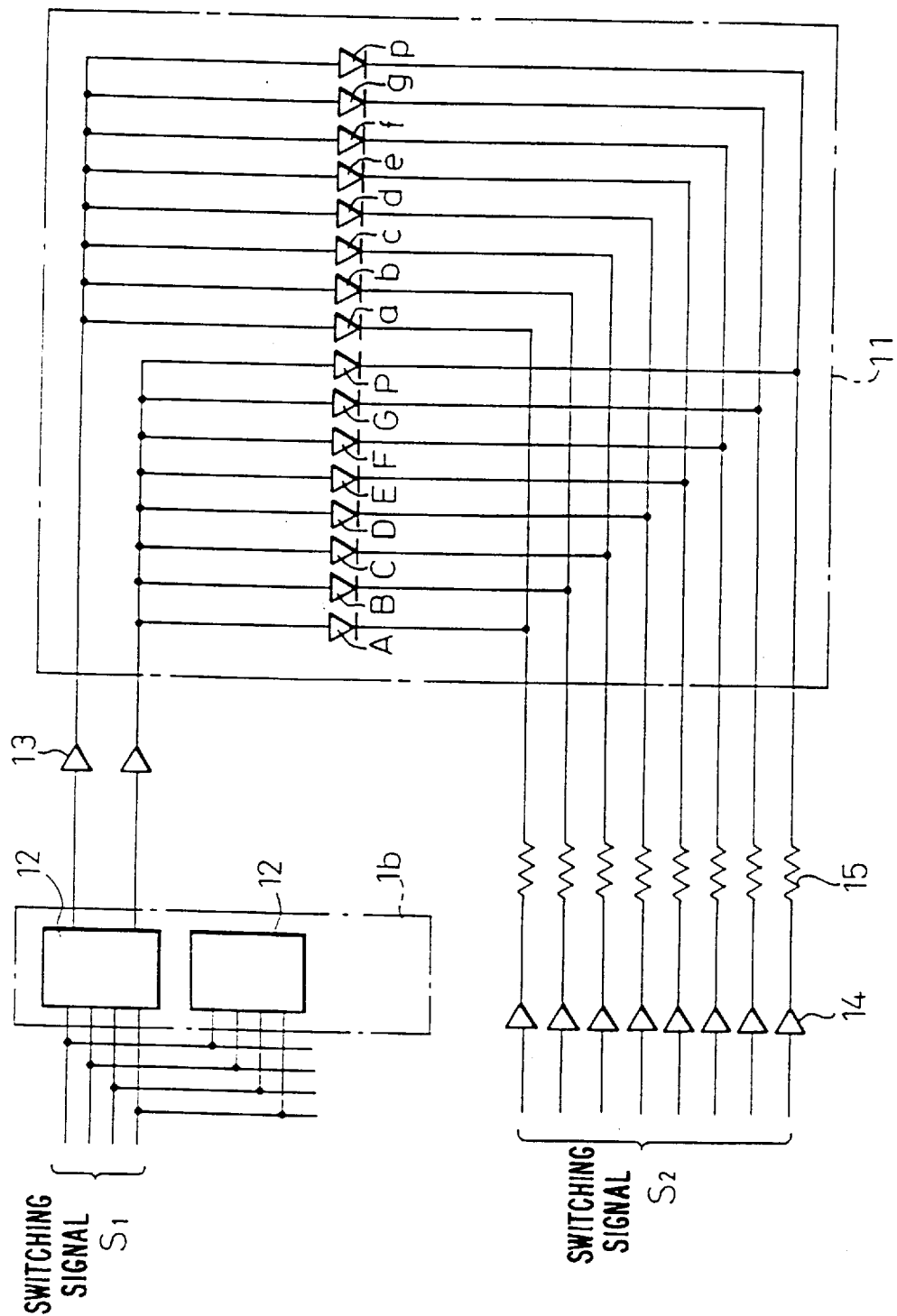

DISPLAY DEVICE IN MEDICAL EXAMINATION AND TREATMENT SYSTEM

BACKGROUND

The present invention concerns the improvement of a display device which displays data necessary for diagnosis and treatment in a medical diagnosis and treatment system.

Various types of medical diagnosis and treatment systems are provided with a display unit which is composed of monochrome display elements such as LEDs; for example, in the case of the pulse oximeter, display is performed in different modes, so that if the measured oxygen saturation level of the patient is normal, the display element is continuously illuminated while the measured value is displayed, and if it deviates from the normal range, the measured value is displayed while the display element flashes. Also, when the settings of the normal range are changed, the inputted setting values are displayed, but since these values are either steadily illuminated or flash, it is difficult to distinguish them clearly from the display when the values are normal or abnormal, resulting in the problem that the possibility of mistaken reading is high.

SUMMARY OF THE INVENTION

The present invention was developed in light of these problems, and has the purpose of offering a display device for a medical diagnosis and treatment system which allows the confirmation of contents or status to be displayed in accordance with these contents or status.

The present invention offers a medical diagnosis and treatment system display device which is provided with a multicolor display unit by which display can be performed in at least 2 colors and a control unit which along with determining whether display is to be performed by continuous illumination or by flashing, in accordance with the diagnostic or therapeutic data to be displayed, displays the diagnostic or therapeutic data by driving the aforesaid multicolor display unit.

By means of the present invention, multiple types of data can be displayed in accordance with the type of color used in a continuous illumination mode, and by adding flashing to this the amount of data which can be displayed is doubled, so that various types of data can be displayed in respectively differing modes. For example, when the multicolor display unit consists of 2 colors, by the combination of display color and steady illumination or flashing display can be performed in 4 modes, so that the 3 statuses of normal and abnormal diagnostic and therapeutic data and setting adjustment values can be easily displayed in differing display modes.

BRIEF DESCRIPTION OF THE DRAWINGS

FIG. 3 is a diagram of the control circuit in this working example.

DESCRIPTION OF THE PREFERRED EMBODIMENTS

Figure 1:
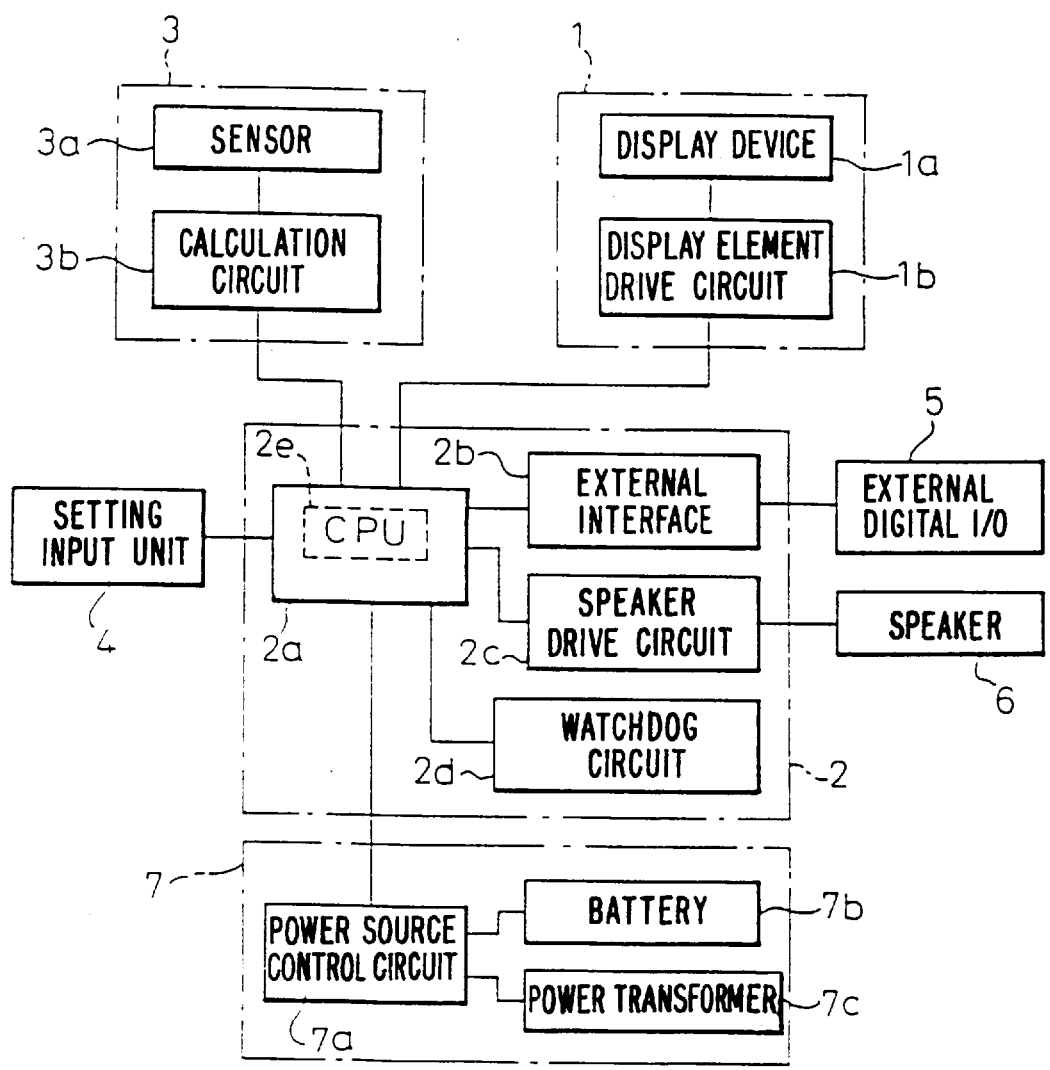
FIG. 1 is a block diagram of the medical diagnosis and treatment system provided with a display device in accordance with one working example of the present invention.
Figure 2:
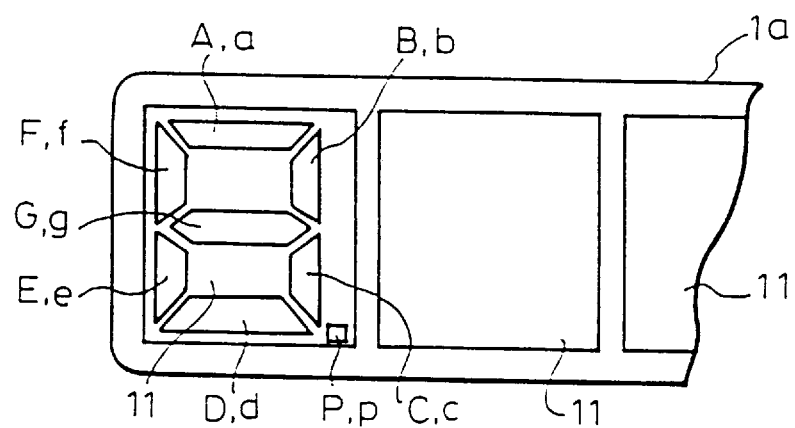
FIG. 2 is a diagram showing the configuration of the display unit of this working example.
Figure 4A:
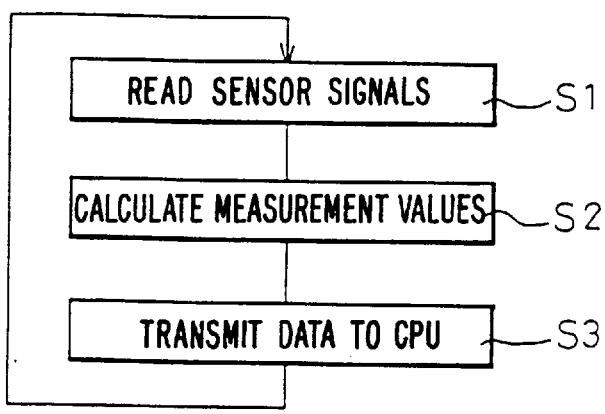
FIGS. 4(a) and 4(b) are flow charts of the operating sequence in this working example.
Figure 4B:
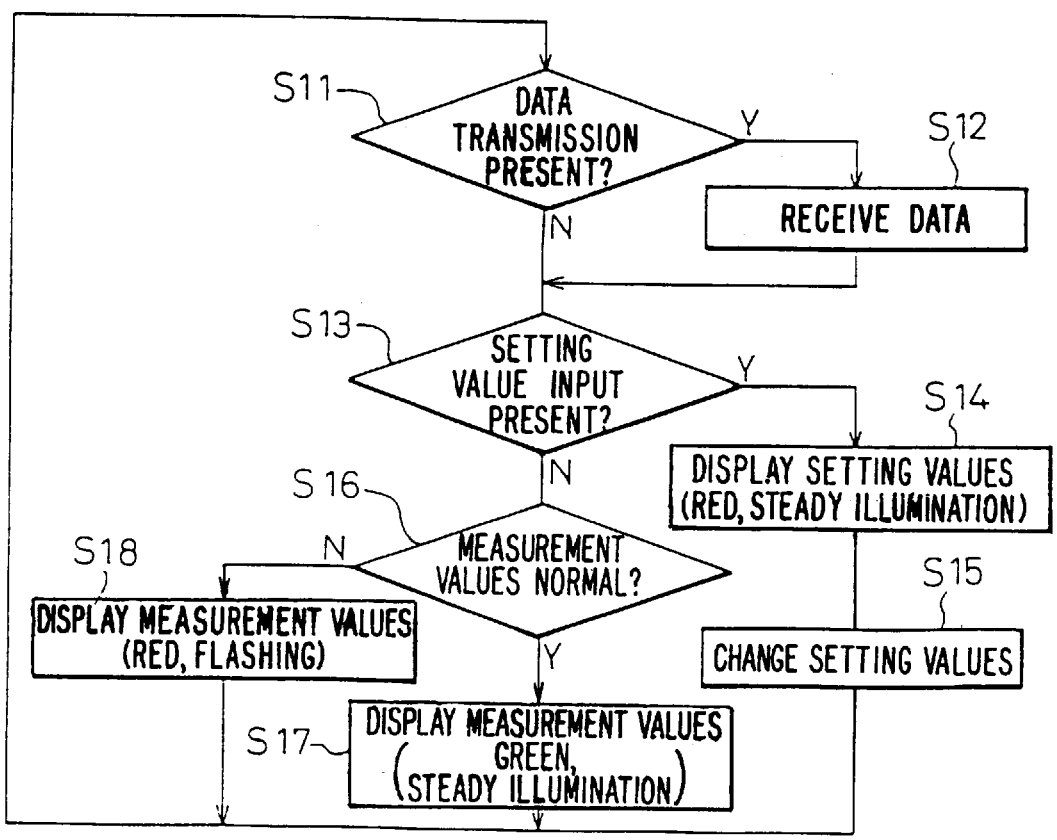

The working example shown in the figures is next explained. FIG. 1 is a block diagram of the medical diagnosis and treatment system provided with a display device of the working example, FIG. 2 is a diagram showing an example of the configuration of the display device, FIG. 3 is a diagram of the control circuit, and FIG. 4 is a flow chart of the operating sequence. The present invention is not limited to the pulse oximeter described above, and can be applied to various types of medical diagnosis and treatment systems. Also, a microcomputer is used in the working example, but the control unit can be constituted so as not to use a microcomputer.

In FIG. 1, the symbol (1) indicates the multicolor display unit, which is composed of a display device (1a) and a display element drive circuit (1b), the symbol (2) indicates the control unit, which is composed of the microcomputer (2a), external interface (2b), speaker drive circuit (2c), watchdog circuit (2d), etc., (2e) is the CPU of the microcomputer (2a), and the control unit (2) performs various control operations such as digital communication with the display or external sources, audio notification, input processing, supervision (run away prevention), etc. Symbol (3) indicates the measurement unit, which is composed of a sensor (3a) for measuring oxygen saturation levels, pulse rate, etc., and a calculation circuit (3b), which converts the signals from the sensor (3a) into measurement data, symbol (4) is a setting value input unit which is composed of switch such as a 10-key pad and a rotary encoder, etc., symbol (5) is an external digital I/O, symbol (6) is a speaker, symbol (7) is a power source unit composed of a power source control circuit (7a), a battery (7b), power transformer (7c), etc.

As shown in FIG. 2, the display device (1a) is composed of multiple LED arrays (11), (11), . . . , which are aggregates of multicolor light-emitting LEDs, the LED arrays (11) are each composed of 8 LEDs, A, B, . . . , G, for emitting red light, and LED a, b, . . . , g for emitting green light, each combined in the same position and arranged in the form of the digital-style number "8". As shown in FIG. 3, the switching signal $S_1$ from the CPU (2e) is decoded by the decoding circuit (12) of the display element drive circuit (1b), the LED arrays to be illuminated and the illumination color, red or green, are selected, and in accordance with the data signal $S_2$ from the CPU (2e), the elements constituting the number "8" configuration which are to be illuminated are selected. Also, (13) is a source driver, (14) is a sync driver, and (15) a damping resistance.

The LED arrays 11, 11, . . . , are switched at a fixed interval, 1.3 ms, for example, by means of a timer, and after all the LEDs are extinguished with all of the data signals $S_2$ from the CPU (2e) as H-level, the selection of the aforesaid LED arrays (11) and the emission color and the selection of the illuminated elements is performed, and switching is performed. Also, flashing is performed by extinguishing all of the LED arrays in a set cycle, and by means of this control, specified LED arrays (11) are illuminated or flashed as red or green, and the measurement values or other data is displayed.

Next, an example of the procedure used in this type of display control is explained based on FIG. 4.

FIG. 4 (a) shows the routine of the measurement unit (3). In switch [step] S1 the analog signals from the sensor (3a) are read by the calculating circuit (3b), in switch [step] S2 the measurement values of the oxygen saturation level, pulse rate, etc., are calculated and converted into digital signals, and in step S3 the measurement data is sequentially transmitted to the CPU (2e).

Step S11 and subsequent steps in FIG. 4 (b) are the routine of the CPU (2e). First, in step S12, it is determined whether there is a data transmission from the measurement unit (3), and if there has been a transmission, this is received (step S12), while if there has been no transmission, the routine moves to the next step S13.

In step S13, it is determined whether there is input from the setting value input unit (4), and if there is any such input, the routine moves to step S14, the setting values which have been inputted are displayed by steady illumination in red, and in step S15 the settings are changed to the new setting values. Also, if there is no setting value input, the process moves to step S16, the transmitted measurement data is compared with the setting values and it is determined whether the measurement values are within normal range; if the values are within normal range, the process moves to step S17, the measurement values are displayed by steady illumination in green, and if they are not within normal range, in step S18 they are displayed by flashing in red. For example, by inputting upper-limit values and lower-limit values as the settings, and designating the interval between the upper-limit and lower-limit values as the normal range, values which do not fall into this range can be considered abnormal.

By means of the aforesaid operations, display of various types of medical diagnosis and treatment data in 3 types of modes is possible, so that when normal data is displayed by steady green illumination, when abnormal data is displayed by read flashing, and measurement values when settings are changed is displayed as continuous red illumination, it is easy to distinguish by the display mode the type of data which is being displayed, and to read the numerical values displayed at this time. Specifically, no longer are the modes in which different types of data or status displayed the same, and not only is the verification of the display facilitated, but the possibility of misreading can be eliminated.

In the working example, the display device (la) is composed of multicolor light-emitting LEDs, but other multicolor display elements such as multicolor-display LCDs may also be used. In addition, the display colors need not be only 2 colors, but may also be 3 colors or multiple color display by means of the combination of 3 primary colors, and in addition and the display can also be made more complex by increasing the color intensity, or changing the flashing cycles, so that when the degree of deviation form normal range is large, this can be distinguished by changing the flashing cycles so that flashing occurs in shorter cycles. Also, in the working example numerical values are displayed, but by using a display device which is able to display letters of symbols other than numbers, the display of various messages, etc., is possible.

Moreover, in combination with the display of normal and abnormal conditions by the display elements as described above, by emitting from a speaker (6) a signal tone or verbal messages which distinguish normal from abnormal conditions, distinguishing these conditions is made even easier.

As is clear from the explanation presented above, the present invention is provided with a multicolor display unit which allows display of at least 2 types of colors, and performs display using display colors and illumination modes according to the type of diagnosis and treatment data to be displayed, specifically, by selecting a steady illumination mode or a flashing mode. Accordingly, by the combination of the display color and illumination mode, different types of data can be displayed in different modes, ambiguity in the display is eliminated, the significance and the contents of the display can be easily confirmed by simple observation, and the ease of use of the medical diagnosis and treatment system is enhanced.

What is claimed is:

1. A pulse oximeter display which displays oxygen saturation data comprising:

a multicolor display unit displaying said oxygen saturation data in first and second colors;

a display drive, coupled to said display unit; and a control unit coupled to said display drive, said control unit being configured to set upper and lower limits for said oxygen saturation data, to compare said oxygen saturation data to said upper and lower limits, to provide a first control signal to said display drive to continuously illuminate said display in said first color in response to said oxygen saturation data being within said limits, to provide a second control signal to said display drive to intermittently illuminate said display unit in said second color if said oxygen saturation data is above said upper limit or below said lower limit, and to provide a third control signal to said display drive to continuously illuminate said display unit in said second color if said limits have not been set.

2. The pulse oximeter of claim 1 wherein said display includes a plurality of data elements, each of said elements having a pair of LEDs in said two different colors, and means for separately activating said LEDs.

3. The pulse oximeter of claim 1 wherein said first color is green and said second color is red.

* * * * *